United States Patent [19]

Schaetzle

[11] Patent Number: 5,687,729
[45] Date of Patent: Nov. 18, 1997

[54] SOURCE OF THERAPEUTIC ACOUSTIC WAVES INTRODUCIBLE INTO THE BODY OF A PATIENT

[75] Inventor: Ulrich Schaetzle, Roettenbach, Germany

[73] Assignee: Siemens Aktiengesellschaft, Munich, Germany

[21] Appl. No.: 493,218

[22] Filed: Jun. 20, 1995

[30] Foreign Application Priority Data

Jun. 22, 1994 [DE] Germany .................. 44 21 795.1

[51] Int. Cl.⁶ .................................................. A61B 8/12
[52] U.S. Cl. .................. 128/660.003; 128/662.005; 604/22; 601/2
[58] Field of Search ................ 607/97; 128/660.3, 128/662.05; 601/1–4; 606/41; 600/2–4; 604/22

[56] References Cited

U.S. PATENT DOCUMENTS

| | | |
|---|---|---|
| 4,710,181 | 12/1987 | Fuqua ........................ 604/104 |
| 4,938,217 | 7/1990 | Lele . |
| 4,955,365 | 9/1990 | Fry et al. . |
| 5,344,435 | 9/1994 | Turner et al. .................. 607/102 |
| 5,365,928 | 11/1994 | Rhinehart et al. ............ 606/197 |
| 5,409,006 | 4/1995 | Buchholtz et al. ............... 601/3 |
| 5,474,071 | 12/1995 | Chapelon et al. ............ 128/662.03 |
| 5,499,630 | 3/1996 | Hiki et al. .................. 128/662.05 |

FOREIGN PATENT DOCUMENTS

| | | |
|---|---|---|
| 0 111 386 | 6/1984 | European Pat. Off. . |
| 0 170 416 | 3/1990 | European Pat. Off. . |

Primary Examiner—Robert L. Nasser
Attorney, Agent, or Firm—Hill, Steadman & Simpson

[57] ABSTRACT

A source of therapeutic acoustic waves for minimally invasive treatment of internal body regions with the therapeutic acoustic waves has a number of source parts which emit the acoustic waves. In order to be able to apply the source easily in the inside of the body in a simple way, source parts are arranged so as to be foldable in an introduction position giving the source a relatively small cross section as viewed in the introduction direction. After introduction into a patient the source parts are unfolded into a working position.

34 Claims, 4 Drawing Sheets

SOURCE OF THERAPEUTIC ACOUSTIC WAVES INTRODUCIBLE INTO THE BODY OF A PATIENT

BACKGROUND OF THE INVENTION

1. Field of the Invention

The present invention is directed to a Source of therapeutic acoustic waves for minimally invasive treatment of internal body regions of a patient with the therapeutic acoustic waves.

2. Description of the Prior Art

Sources of therapeutic acoustic waves of the above type are utilized, for example, for treating benign as well as malignant tissue modifications. Such sources thereby usually emit acoustic waves in the ultrasound range. The different therapy forms utilize the thermal effect of ultrasound waves. Temperatures in the range from 40°–100° C. can be generated in the focus during the treatment in the case of focused acoustic waves, whereby the temperature is selected dependent on the type of pathological condition to be treated.

Sources of this type are employed, for example, for treating benign prostate hyperplasia (BPH). Sources used in such treatment are fashioned for rectal application. In order to avoid injury to the anus, the cross sectional dimensions of the source cannot exceed certain maximum dimensions. This presents the problem that the emission surface available for the emission of the therapeutic acoustic waves is limited. Since only a certain maximum acoustic power can be emitted per unit of area, the acoustic power that can be emitted overall is thus limited. This results in an undesirably long duration for the treatment. Similar problems arise if the source is applied through a trocar, for example during the course of a laparascopic intervention.

U.S. Pat. No. 4,955,365 discloses a source of the type initially cited that is provided for the treatment of BPH. This source has a single active source part, i.e. a source part that serves the purpose of generating therapeutic acoustic waves. The therapeutic acoustic waves generated by this source part are deflected in the manner required for a given application with an acoustic mirror. In order to facilitate the introduction of the source into the interior of the body, there is the possibility of pivoting the source part and the mirror such that reduced cross sectional dimensions are achieved. A certain improvement is thus achieved; however, the acoustic power that can be emitted is still to be limited.

SUMMARY OF THE INVENTION

An object of the present invention is to provide a source of therapeutic acoustic waves that can be easily applied in the interior of the body but which is nonetheless capable of emitting a high acoustic power.

This object is inventively achieved is a source of therapeutic acoustic waves introducible into the body of a life form for minimally invasive treatment of internal body regions with the therapeutic acoustic waves which is subdivided into at least two source parts serving the purpose of generating the therapeutic acoustic waves, and which can be folded such that the source parts are adjustable from a folded introduction position into an unfolded working position and vice versa. The source has reduced cross sectional dimensions in the introduction position compared to the working position. It is thus possible to apply the source in a natural way in its folded condition, for example rectally or transesophagously or in an transcutaneously way, for example through a trocar, and then to unfold it in the interior of the body so that an active emission surface for the therapeutic acoustic waves, which that can be substantially larger than in the case of a non-foldable source that is applied in an identical way, is available in the unfolded condition as a consequence of the fact that all source parts actively participate in the generation of the therapeutic acoustic waves.

European Application 0 111 386 discloses a source of therapeutic acoustic waves that is subdivided into a plurality of source parts which can be pivoted relative to one another within certain limits for influencing the position of the focus of the therapeutic acoustic waves. This source, however, is not introducible into the body of a living subject.

According to a preferred embodiment of the invention, an especially beneficial and structurally simple format is achieved by connecting the source parts to one another so as to be pivotable around an axis that proceeds substantially parallel to the introduction direction for the purpose of adjusting the source parts from the introduction into the working position and vice versa. This results in the smallest describable circle that can be drawn around the cross section of the source in introduction position, as viewed in the introduction direction, having a significantly smaller diameter than the smallest describable circle of the cross section of the source in working position. A "significantly smaller diameter" means a diameter that is at most equal to 0.6 times the diameter applicable in the working position.

In order to have an optimally large emission surface available in the working position for a given diameter of the source in the introduction position, in a preferred modification of the invention the source is formed by at least three source parts.

When the source has three source parts that, as seen in the introduction direction, are arranged in the form of a preferably isosceles, particularly equilateral triangle in the introduction position, the technical outlay for adjusting the source from its introduction position into its working position and vice versa is still relatively slight, even though the emission surface available in working position is approximately three times as large as in the case of a non-foldable source whose cross sectional dimensions in the introduction position correspond to those of the inventive source.

Particularly in view of the application of the source using natural body paths, it is advantageous for the source to have a rounded cross sectional contour in the introduction position as soon in the introduction direction in order to prevent a patient suffering pain or injury.

In order to be able to concentrate the effect of the therapeutic acoustic waves onto those regions that in fact require treatment, in one version of the invention focused therapeutic acoustic waves can be emitted with the source, with the therapeutic acoustic waves emanating from different source parts converging in a common focus zone in order to assure an optimally short treatment duration.

When the source is implemented as an ultrasound transducer, particularly a piezoelectric ultrasound transducer, in one embodiment of the invention the ultrasound transducer is constructed as an array, especially as a liner array of a plurality of ultrasound transducer elements. Problems occurring in the manufacture of larger ultrasound transducers are thus avoided and there is the possibility, when driving the ultrasound transducer elements in the fashion of a phased array to displace the focus zone of the therapeutic acoustic waves relative to the source. It is then possible to treat different areas without a displacement of the source itself being required. As a result of the drive of the ultrasound transducer elements in the fashion of a phased array, moreover, there is also the possibility of varying the size of the focus zone.

In order to have further information available in addition to the image information that, for example, can be acquired with the assistance of a standard endoscope regarding the position of the source relative to the region to be treated, in a preferred embodiment of the invention that diagnostic ultrasound waves for ultrasound imaging can be optionally emitted with the source instead of therapeutic acoustic waves. It may be adequate under certain circumstances, because of the lower power consumption in the emission of diagnostic waves, for only one source part to be activatable for the emission of diagnostic ultrasound waves. There is then thus the possibility of observing the region to be treated in an ultrasound image. It is advantageous in this context to mix a mark indicating the position of the focus zone mixed into the generated ultrasound image, since there is then always certainty regarding what body region will be charged with the waves upon activation of the source to emit therapeutic acoustic waves.

According to one embodiment of the invention, a needle guide for a biopsy needle is attached to the source. There is thus the possibility of being able to take tissue samples as needed. In order to be able to designationally take a tissue sample from an especially interesting area, it is provided in a further version of the invention to mix mark indicating the course (path) of the paracentesis channel of the biopsy needle into the generated ultrasound image. There is thus the possibility of initially aligning the needle guide such that the mark indicating the paracentesis channel proceeds through the region of the interest and the biopsy needle is then introduced through the needle guide for taking the tissue sample.

There is also the possibility of bringing thermoelements into the region to be treated using a biopsy needle in order to be able to measure the temperatures which arise in the region during the treatment with the therapeutic acoustic waves.

In order to be able to position the source already located in the inside of the body in accord with the necessities of a particular application, in another embodiment of the invention a handle is attached to the source in an articulated fashion. The needle guide may also be attached to the handle. There is then the possibility of bringing the needle guide into the position suitable for the tissue-taking to be implemented by adjusting the handle relative to the source. The needle, by the way, may be part of the source, especially if a custom made needle is used. On the other hand, the needle also may be not a part of the source, if a usual needle is used.

DESCRIPTION OF THE PREFERRED EMBODIMENTS

The inventive therapeutic acoustic wave source 1 shown in FIGS. 1–5 is foldably fashioned and contains three acoustic wave source parts 1a–1c. The source parts 1b and 1c are pivotably attached to the source part 1a, such that the source 1 can be selectively placed in a folded position illustrated in FIGS. 1 and 2, which is referred to below as the introduction position, or in an unfolded position shown in FIGS. 3 and 4, which is referred to below as working position.

The source parts 1b and 1c are respectively pivotably connected to the source part 1a with two hinge-like articulations 2A and 2b. The source parts 1b and 1c are pivotable around respective axes $A_1$ and $A_2$ proceeding essentially parallel to the introduction direction illustrated by an arrow referenced E.

Figure 2:
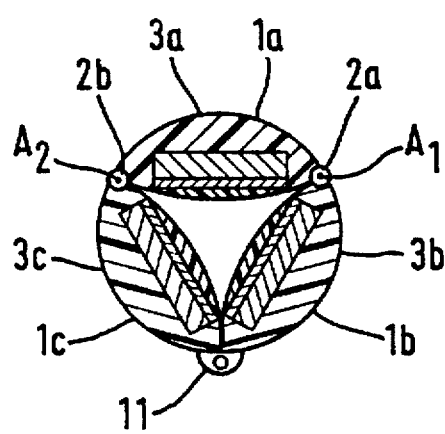
FIG. 2 is a cross-sectional view of the source of FIG. 1 taken along the line 11—11 in FIG. 1.

As can be seen from FIG. 2, the source parts 1a–1c—as viewed in the introduction direction—are arranged in the form of an isosceles triangle, in this embodiment in the form of an equilateral triangle, when the source is in its introduction position. The exteriors of the source parts 1a–1c are shaped such that the source 1 has a rounded, preferably circular, cross-sectional (peripheral) contour in the introduction position, likewise viewed in the introduction direction. In the case of the exemplary embodiment set forth, the smallest circle describable around the source I in the introduction position, and which corresponds to the cross-sectional contour introduction position, has a diameter of approximately 15 mm. In the working position, the smallest circle that can be circumscribed around the source, which is partially indicated in FIG. 4 as dashed line K, has a diameter of approximately 35 mm. The diameter of the smallest circle circumscribable around the source I in the introduction position is thus significantly smaller than the diameter of the smallest circle circumscribable around the source 1 in the working position, since the former diameter is less than half as large as the latter diameter.

The source parts 1a–1c have respective a base members 3a–3c each preferably formed of physiologically compatible plastic in which a respective ultrasound transducer 5a–5c attached to a backing 4a–4c is embedded. The ultrasound transducers 5a–5c are piezoelectric ultrasound transducers. The thickness of the backing 4a–4c and the acoustic impedance of its material are selected in a known way for matching the natural frequency of the ultrasound transducers (for example, 2 MHz) and matching the acoustic impedance of the material of the ultrasound transducers 5a–5c. The ultrasound transducers 5a–5c are respectively provided with acoustic positive lenses 6a–6c, so that a focusing of the ultrasound waves emanating from the ultrasound transducers 5a–5c onto a line focus proceeding parallel to the longitudinal axis of the respective ultrasound transducers 5a–5c theoretically arise as shown with dot-dashed lines in FIG. 4. The source parts 1a–1c, moreover, are arranged in the working position of the source 1 so that the line foci coincide to form a common line focus LF of the source parts 1a–1c.

Figure 5:
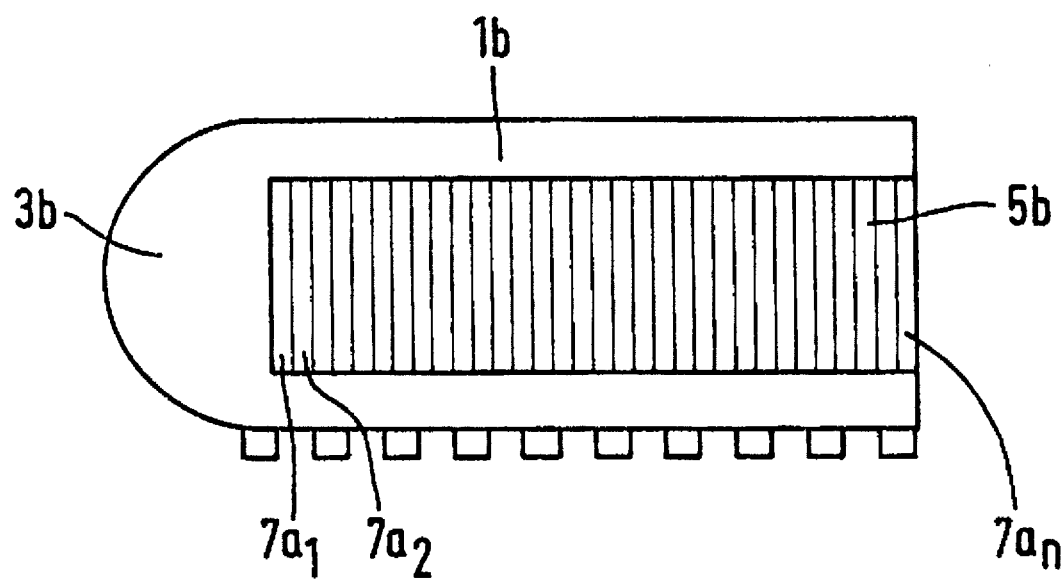
FIG. 5 a view of a detail of the source of FIGS. 1-4.

As shown in FIG. 5 on the basis of the example of the source part 1b shown without positive lens 6b, the source parts 1a–1c, i.e. their ultrasound transducers 5a–5c, are divided into a number of ultrasound transducer elements in the fashion of a liner array (linear arrangement). The ultrasound transducer elements are referenced $7a_1$–$7a_n$. In the exemplary embodiment set forth, moreover, the ultrasound transducers 5a–5c together with the backings 4a–4c and the positive lenses 6a–6c are identically fashioned; however, this need not necessarily be the case.

Figure 3:
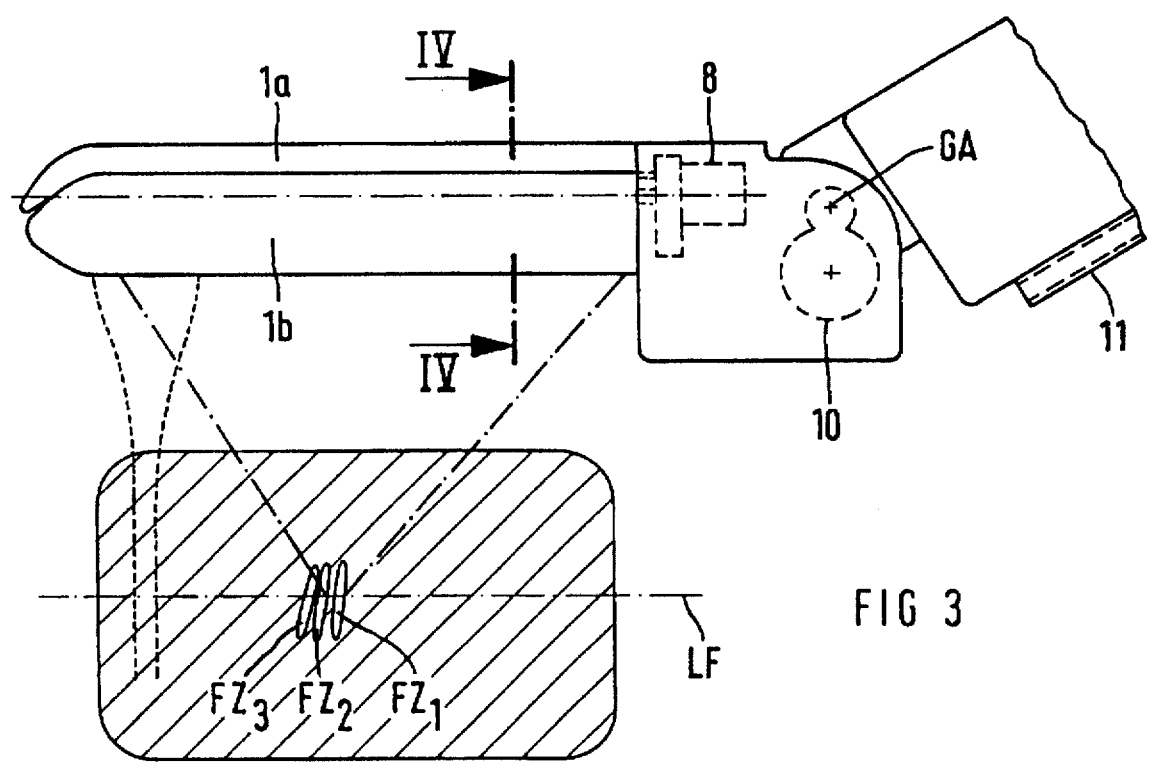
FIG. 3 is a side view of the source of FIGS. 1 and 2 in its unfolded condition.
Figure 4:
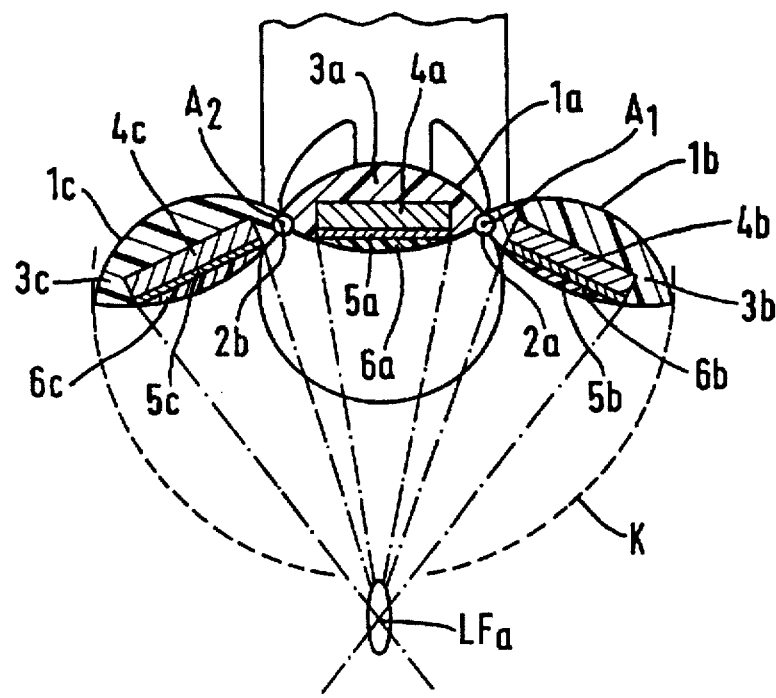
FIG. 4 is a cross-sectional view of the unfolded source of FIG. 3 along line IV—IV in FIG. 3.

The ultrasound transducer elements of the source parts 1a–1c are driven during operation of the source 1 in the fashion of phased arrays (i.e., the arrangement is driven with a phase-offset) so that a common, approximately cigar-shaped focus zone arises for the ultrasound waves emanating from the ultrasound transducers 5a–5c. Dependent on the drive of the ultrasound transducer elements, the focus zone can be displaced relative to the source I within a region identified in FIG. 3 by shading. Three possible position of the focus zone $FZ_1$–$FZ_3$ are indicated in FIG. 3. As used herein, focus zone means a region that surrounds the location of maximum acoustic pressure and that is limited by a three-dimensional −3 dB isobaric surface. This region is also referred to as the region of therapeutic action.

There is also the possibility of optionally activating one of the source parts, such as the ultrasound transducer 5a of the source part 1a, to emit diagnostic ultrasound, such that can an area can be displayed in an ultrasound image which at least contains that region within which the focus zone can be displaced. The ultrasound transducer elements of the ultrasound transducer 5a are thereby driven in the manner of a linear scan as is known in diagnostic ultrasound technology. Since a group of ultrasound transducer elements is thereby always driven in common in a known way, the contour of the diagnostic ultrasound beam (shown as a dot-dash line for example in FIG. 3) arises for a scan position of the linear scan in the plane shown in FIG. 3.

In order to be able to adjust the source I from its introduction position into its working position and vice versa, an electromechanical gear motor 8 acting on the source part 1b and 1c is provided.

Figure 1:
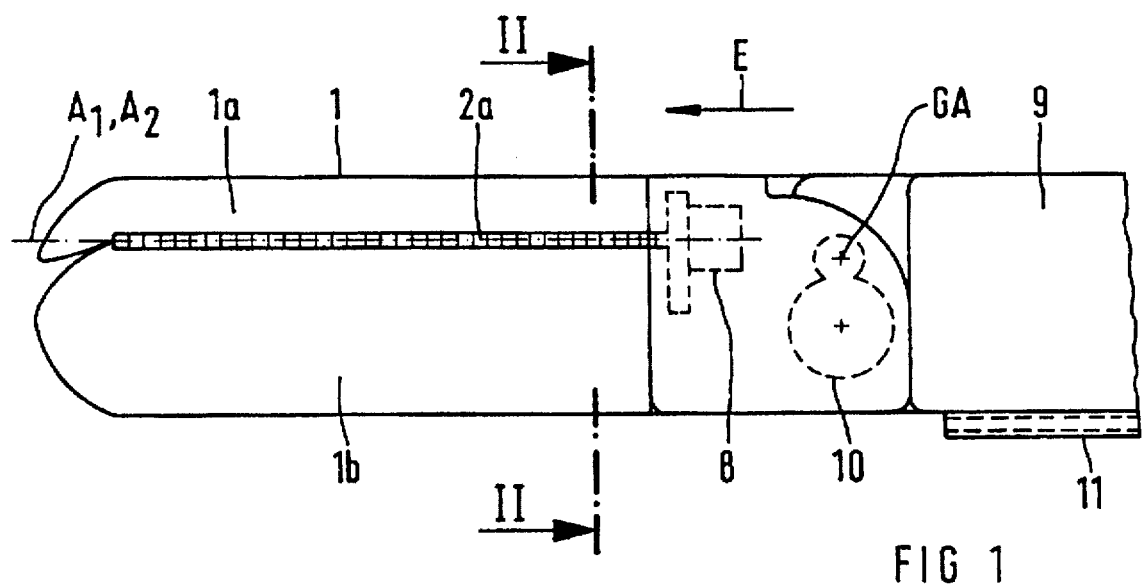
FIG. 1 is a side view of a therapeutic acoustic wave source constructed in accordance with the principles of the present invention in its folded condition.

A handle 9 is attached in articulated fashion to the source 1, namely such that it is pivotable around an articulated axle that proceeds at a right angle relative to the plane of the drawing and is referenced GA in FIGS. 1 and 3. The swivel motion can be implemented motor-driven. To this end, a further electromechanical gear motor 10 indicated with dashed lines in FIGS. 1 and 3 is provided.

The handle 9, moreover, is provided with a needle guide 11 for a biopsy needle 12 or the like.

Figure 6:
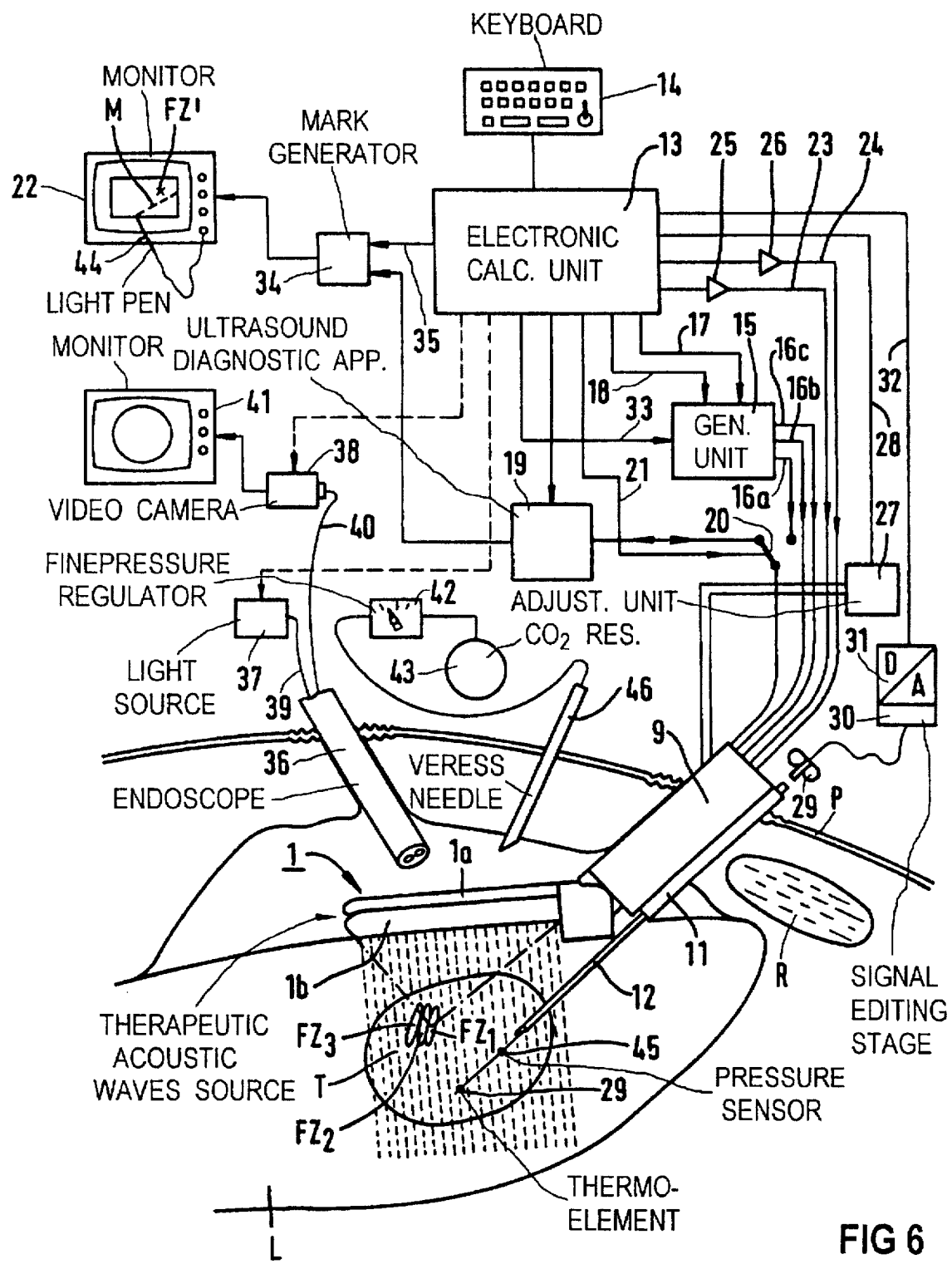
FIG. 6 illustrates the treatment of a tumor with an apparatus containing an inventive source with relevant operating components shown in a block circuit diagram.

FIG. 6 shows a therapy apparatus for the treatment of pathological tissue modifications which contains an inventive source 1.

The apparatus includes an electronic calculation unit 13 having a connected keyboard 14 that serve the purpose of controlling and operating the therapy apparatus.

An electrical generator unit 15 is also provided, this serving the purpose of driving the ultrasound transducers 5a–5c to generate therapeutic ultrasound. The generator unit 15 is connected to the ultrasound transducers 5a, 5b, 5c via respective lines 16a, 16b, 16c. The generator unit 15 is also connected to the electronic calculating unit 13 via two control lines 17 and 18. Via the control line 17, the electronic calculating unit 13 activates the generator unit 15 so that therapeutic ultrasound is emitted as long as a corresponding signal is present on the control line 17. The control line 18 serves the purpose of setting the position of the focus zone in the required way.

An ultrasound diagnostics apparatus 19 is also provided; this can be selectively connectable to the ultrasound transducer 5a instead of the corresponding output of the generator unit 15. The selected connection is made via a switch 20 actuated by the electronic calculating unit 13. When the switch 20 assumes the position shown in FIG. 6, the ultrasound diagnostic apparatus 19 collaborates with the ultrasound transducer 5a in a known way such that ultrasound B-images are generated by a linear scan, so that a region to be treated is displayed on a monitor 22 in the form of an ultrasound image.

In order to be able to adjust the source I from its introduction position into its working position and vice versa, as well as to be able to adjust the inclination of the handle 9 relative to the source 11, the corresponding gear motors 8 and 10 are connected to the electronic calculating unit 13 via respective control lines 23 and 24, with suitable driver stages 25 and 26 respectively connected to the control lines 23 and 24.

Moreover, a schematically indicated adjustment unit 27 is provided, serving the purpose of adjusting the position of the source 1 relative to a patient P, preferably three-dimensionally, proceeding from a manually set initial position under motor drive within certain limits. The adjustment unit 27 is in communication with the electronic calculating unit 13 via a control line 28.

In order to be able to undertake temperature measurements in the region to be treated, a temperature sensor, namely a thermal element 29, is provided, this being in communication with an analog-to-digital converter 31 via a signal editing stage 30. The output data of the analog-to-digital converter 31 are supplied to the electronic calculating unit 13 via a data line 32. The data from the analog-to-digital converter 31 are employed by the electronic calculating unit 13 in order to regulate the intensity of the therapeutic ultrasound waves via a control line 33 leading to the generator unit 15 or in order to interrupt the generation of the therapeutic ultrasound waves via the control line 17 when necessary.

The output signals of the ultrasound diagnostic apparatus 19 corresponding to the generated ultrasound images are not directly supplied to the monitor 22, but are supplied through a mark generator 34. The mark generator 34 mixes a mark FZ' into the ultrasound image that corresponds to the momentary (current) position of the focus zone FZ in the ultrasound image. The mark generator 34 also mixes a line-shaped mark M into the ultrasound image that indicates the course of the paracentesis channel of a biopsy needle (if used) accepted in the needle guide 11.

The mark generator 34 receives the information required for the positionally correct mixing-in of the marks M and FZ' via a line 35 from the electronic calculating unit 13. The electronic calculating unit 13 derives the information with respect to the mark FZ' from the signals supplied to the generator unit 15 for focusing the therapeutic ultrasound waves. The information with respect to the position of the mark M is acquired by the electronic calculating unit 13 from a signal from a position sensor (not shown) allocated to the gear motor 10 that emits a signal to the electronic calculating unit 13 corresponding to the angular position of the handle 9 relative to the source 1.

FIG. 6 shows the treatment of a tumor T in the liver L of a patient P.

For the implementation of the treatment, the abdominal cavity is first filled with $CO_2$ via a Veress needle 46. The $CO_2$ insufflator is shown as a $CO_2$ reservoir 32 and fine-pressure control 42. An endoscope 36 is subsequently applied. A rib is indicated in FIG. 6 and is referenced R. The endoscope 36 is guided into the abdominal cavity of the patient P through a trocar that is not shown in FIG. 6. The application of the source 1 also ensues through a trocar of a suitable size which is likewise not shown in FIG. 6.

The endoscope 36 has a light source 37 and a video camera 38 that are optically connected to the end of the endoscope 36 in a known arrangement, preferably via fiber-optical light waveguides 39 and 40. The image of the video camera 38 is displayed on a monitor 41.

By observation through the endoscope 36, it is possible to first suitably position the source 1, while angling the handle 9 as required, and to then unfold it. Subsequently, the source part 1a is activated to emit diagnostic ultrasound waves and to receive the corresponding echoes in order to obtain a corresponding ultrasound image on the monitor 22. Preferably given the assistance of the motor-driven adjustment means 27, the source 1 is now positioned such that the tumor T clearly appears in the ultrasound image and the mark M proceeds through the tumor T in the desired way, whereby slight corrections are possible by modifying the angular position between source 1 and handle 9.

If desired, a tissue sample can now be taken with a biopsy needle introduced through the needle guide 11 under diagnostic ultrasound control. Additionally or alternatively, the thermal element 29 is placed in the tumor T at a suitable location with a puncture needle 12.

Subsequently, a region to be treated is marked in the ultrasound image with a light pen 44.

In response to a corresponding actuation of the keyboard 14, therapeutic ultrasound waves are then emitted for a time selectable with the keyboard 14 and having an intensity that can likewise be preselected with the keyboard. The ultrasound transducer elements of the source 1 are thereby driven such that the focus zone of the therapeutic ultrasound waves is located at that location of the tumor T which corresponds to the location identified in the ultrasound image with the light pen 44.

If a temperature is measured with the thermal element 29 before the expiration of the time duration set with the keyboard, which upwardly exceeds an upper limit that can be entered with the keyboard 14, the intensity of the therapeutic ultrasound waves is initially reduced and, insofar as the temperature measured with the thermal element 29 still continues to exceed the limit value, the emission of therapeutic ultrasound is interrupted.

There is always the possibility of marking a larger area with the light pen 44, this then being treated step-by-step in response to a corresponding actuation of the keyboard 14 with the electronic calculating unit 13 causing displacement of the focus zone little by little until the entire marked region has been treated.

After the implementation of the treatment, the source 1 is folded from its working position back into its introduction position and if the handle 9 was angled, it is reset to be straight. The source 1 can then be removed.

A pressure measurement can also ensue in addition to the temperature measurement. This is indicated in FIG. 6 in that a miniaturized pressure sensor 45 introducible with the puncture needle 12 is also provided. The pressure sensor 45, for example, can be a sensor constructed of a piezoelectrically activated polymer film.

Although modifications and changes may be suggested by those skilled in the art, it is the intention of the inventors to embody within the patent warranted hereon all changes and modifications as reasonably and properly come within the scope of their contribution to the art.

I claim as my invention:

1. A source of therapeutic acoustic waves comprising:
   at least two source elements each emitting therapeutic acoustic waves;
   an instrument on which said at least two source elements are mounted adapted for introducing said at least two source elements into a body of a patient; and
   means for mounting said at least two source elements on said instrument for permitting movement of said at least two source elements between an introduction position wherein said at least two source elements are relatively rotatably folded together in a first configuration and a working position wherein said at least two source elements are relatively rotatably unfolded in a second configuration, and vice versa, said first configuration having cross-sectional dimensions which are smaller than cross-sectional dimensions of said second configuration.

2. A source as claimed in claim 1 wherein said instrument has an introduction direction along which said instrument is adapted for introduction into said patient, and wherein said means for mounting said at least two source elements comprises means for pivotably connecting said at least two source elements for folding said at least two source elements around an axis proceeding substantially parallel to said introduction direction.

3. A source as claimed in claim 1 wherein said at least two source elements in said introduction position have a first cross section and wherein said at least two source elements in said working position have a second cross section, and wherein a smallest circle circumscribable around said first cross section has a smaller diameter than a smallest circle circumscribable around said second cross section.

4. A source as claimed in claim 1 comprising three of said source elements.

5. A source as claimed in claim 4 wherein said instrument has an introduction direction along which said instrument is adapted for introduction into said patient, and wherein said three source elements, as seen in said introduction direction, are disposed to form an isosceles triangle.

6. A source as claimed in claim 5 wherein said three source elements are disposed to form an equilateral triangle as seen in said introduction direction.

7. A source as claimed in claim 1 wherein said instrument has an introduction direction along which said instrument is adapted for introduction into said patient, and wherein said instrument with said at least two source elements mounted thereon in said introduction position has a rounded exterior cross-sectional contour as seen in said introduction direction.

8. A source as claimed in claim 1 wherein each of said at least two source elements emits focussed therapeutic acoustic waves.

9. A source as claimed in claim 8 wherein said at least two source elements respectively emit therapeutic acoustic waves which converge in a common focus zone.

10. A source as claimed in claim 9, wherein said at least two source elements are mounted on said instrument for allowing said therapeutic acoustic waves to converge in said common focus zone.

11. A source as claimed in claim 1 wherein each of said at least two source elements comprises an array of a plurality of piezoelectric ultrasound transducer elements.

12. A source as claimed in claim 11 wherein said array comprises a linear array.

13. A source as claimed in claim 11 further comprising means for driving each array as a phased array.

14. A source as claimed in claim 1 wherein each of said at least two source elements comprises a source element emitting focussed therapeutic acoustic waves converging in a common focus zone, and means for displacing said focus zone relative to said instrument.

15. A source as claimed in claim 1 further comprising means for selectively operating at least one of said source elements for emitting diagnostic ultrasound waves or said therapeutic acoustic waves.

16. A source as claimed in claim 15 wherein said means for selectively operating said source elements comprises means for operating only one of said source elements for selectively emitting diagnostic ultrasound waves or said therapeutic acoustic waves.

17. A source as claimed in claim 15 further comprising means for generating an ultrasound image from diagnostic ultrasound waves emitted by said at least one source element which are reflected by said patient, and wherein said source elements, in combination, comprise means for emitting said therapeutic acoustic waves converging in a common focus zone, and further comprising means for mixing a mark into said ultrasound image identifying a current position of said focus zone.

18. A source as claimed in claim 17 further comprising a needle guide attached to said source for inserting a needle into an organ of said patient.

19. A source as claimed in claim 18 comprising means for mixing a further mark into said ultrasound image identifying a path of said needle in said organ.

20. A source as claimed in claim 1 further comprising a needle guide attached to said source for inserting a needle into an organ in said patient.

21. A source as claimed in claim 20 wherein said instrument comprises a handle and wherein said needle guide is attached to said handle.

22. A source as claimed in claim 1 wherein said instrument comprises a body portion on which said at least two source elements are mounted, and a handle attached to said body portion by an articulated connection.

23. A source as claimed in claim 22 further comprising a needle and a needle guide attached to said handle for inserting a needle into an organ in said patient.

24. A source as claimed in claim 1, wherein said instrument comprises a handle.

25. A source as claimed in claim 24, wherein said handle is connected to said instrument by an articulated connection.

26. An apparatus for treating internal body regions with focused therapeutic acoustic waves, comprising:

a source of therapeutic acoustic waves adapted for introduction into a body of a patient having a plurality of source elements movable between an introduction position wherein said source elements are relatively rotatably folded together in a first configuration and a working position wherein said source elements are relatively rotatably unfolded in a second configuration, said first configuration having cross-sectional dimensions which are smaller than cross-sectional dimensions of said second configuration;

means for driving said source for emitting therapeutic acoustic waves converging at a focus zone;

means for driving said source for generating diagnostic ultrasound waves and for receiving corresponding ultrasound echoes from said patient for producing ultrasound images of said patient, and including means for mixing a mark into said ultrasound images identifying a current position of said focus zone; and means for adjusting a position of said focus zone for causing said focus zone to coincide with a region of said patient to be treated.

27. An apparatus as claimed in claim 26 further comprising an endoscope adapted for insertion into the body of said patient for monitoring application of said source in the interior of the body of the patient.

28. An apparatus as claimed in claim 26 further comprising a needle and a needle guide attached to said source.

29. An apparatus as claimed in claim 28 further comprising means for mixing a further mark into said ultrasound images identifying a path of said needle in said patient.

30. An apparatus as claimed in claim 26 further comprising a pressure sensor and a needle adapted for introducing said pressure sensor into the body of said patient in a region to be treated by said therapeutic acoustic waves, and means for controlling said means for driving said source to generate said therapeutic acoustic waves dependent on pressure sensed by said pressure sensor.

31. An apparatus as claimed in claim 26 further comprising a temperature sensor and a needle adapted for introducing said temperature sensor into the body of said patient in a region to be treated by said therapeutic acoustic waves, and means for controlling said means for driving said source to generate said therapeutic acoustic waves dependent on temperature sensed by said temperature sensor.

32. An apparatus as claimed in claim 26 further comprising a pressure sensor, a temperature sensor, and a needle adapted for introducing said pressure sensor and said temperature sensor into the body of said patient in a region to be treated by said therapeutic acoustic waves, and means for controlling said means for driving said source for generating said therapeutic acoustic waves dependent on pressure and temperature respectively sensed by said pressure sensor and said temperature sensor.

33. An apparatus as claimed in claim 26 wherein said source is adapted for insertion into a body cavity in said patient, and said apparatus further comprising means for filling said body cavity with an acoustic propagation medium.

34. An apparatus as claimed in claim 26 further comprising means for filling a body accepting the source with an acoustic propagation medium.

* * * * *